(12) United States Patent
Ansorge et al.

(10) Patent No.: US 7,425,532 B2
(45) Date of Patent: Sep. 16, 2008

(54) USE OF ALANYL AMINOPEPTIDASE INHIBITORS AND PHARMACEUTICAL COMPOSITIONS CONTAINING SAID INHIBITORS

(75) Inventors: Siegfried Ansorge, Hohenwarthe (DE); Janine Tadje, Magdeburg (DE); Uwe Lendeckel, Magdeburg (DE)

(73) Assignee: IMTM GmbH, Magdeburg (DE)

( * ) Notice: Subject to any disclaimer, the term of this patent is extended or adjusted under 35 U.S.C. 154(b) by 0 days.

(21) Appl. No.: 10/520,014

(22) PCT Filed: Jul. 4, 2003

(86) PCT No.: PCT/EP03/07199

§ 371 (c)(1),
(2), (4) Date: Mar. 6, 2006

(87) PCT Pub. No.: WO2004/004750

PCT Pub. Date: Jan. 15, 2004

(65) Prior Publication Data

US 2006/0211602 A1   Sep. 21, 2006

(30) Foreign Application Priority Data

Jul. 5, 2002  (DE) .................. 102 30 381

(51) Int. Cl.
*A61K 38/05* (2006.01)
*A61K 31/495* (2006.01)

(52) U.S. Cl. .................. 514/2; 514/247

(58) Field of Classification Search .......... None
See application file for complete search history.

(56) References Cited

U.S. PATENT DOCUMENTS

2006/0040850 A1 * 2/2006 Ansorge et al. ............. 514/2

FOREIGN PATENT DOCUMENTS

| DE | 101 00 052 A 1 | 7/2002 | |
|----|----|----|----|
| JP | 10310599 | * | 11/1998 |
| JP | 410310599 A | * | 11/1998 |
| WO | WO 91/08760 | | 6/1991 |
| WO | WO 95/04533 | | 2/1995 |
| WO | WO 96/12737 | | 5/1996 |
| WO | WO 01/54707 A2 | | 8/2001 |
| WO | WO 01/89569 A1 | | 11/2001 |

OTHER PUBLICATIONS

Lendeckel et al., "Inhibition of alanyl aminopeptidase induces MAP-kinase p42/ERK2 in the human T cell line KARPAS-299," Biochem. Biophys. Res. Comm., 1998, 252, 5-9.*
Kakuta et al. "Novel specific puromycin-sensitive aminopeptidase inhibitors: 3-(2,6-diethylphenyl)-2,4(1H,3H)-quinazolinedione and N-(2,6-diethylphenyl)-2-amino-4H-3,1-benzoxazin-4-one," Heterocycles, 2001, 55, 1433, abstract only.*
Sharabi et al. "A peptide based on the complementarity-determining region 1 of an autoantibody ameliorates lupus by up-regulating CD4+CD25+ cells and TGF-beta." PNAS, 2006, 103, 8810-5.*
Youn et al. "Metallothionein suppresses collagen-induced arthritis via induction of TGF-beta and down-regulation of proinflammatory mediators." Clin. Exp. Immunol., 2002, 129, 232-9.*
Le et al. "The immunopharmacological properties of transforming growth factor beta." Int. Immunopharm., 2005, 5, 1771-82.*
Ansorge, et al.; Dipeptidyl Peptidase IV/CD26 and Aminopeptidase N/CD13 in Regulation of the Immune Response; In: International Congress Series, 2001, 1218 (Cell-Surface Aminopeptidases: Basic and Clinical Aspects), pp. 85-94.

* cited by examiner

*Primary Examiner*—Cecilia Tsang
*Assistant Examiner*—Christina Marchetti Bradley
(74) *Attorney, Agent, or Firm*—Hodgson Russ LLP

(57) ABSTRACT

The present invention relates to the use of one inhibitor or of several inhibitors of alanyl aminopeptidases and/or of enzymes having a similar substrate specificity for the induction of the production of TGF-β1 and of the expression of TGF-β1 in and/or on Treg cells and relates to the use for preventing and/or treating autoimmune diseases, allergies, arteriosclerosis and for suppressing graft rejection reactions. The invention furthermore relates to uses, wherein peptide fragments of pathogenic autoantigens or synthetic analogs and/or specific antigenic components of pathogenic microorganisms are used in addition.

9 Claims, 5 Drawing Sheets

Figure 1: Induction of the surface expression of TGF-β1 on human regulatory T-lymphocytes Figure 2: Induction of the TGF-$\beta$1 mRNA expression in human regulatory T-lymphocytes Figure 3: Induction of the TGF-$\beta$1 mRNA expression in human regulatory T-lymphocytes Figure 4: Induction of the TGF-β1 mRNA expression in human regulatory T-lymphocytes

USE OF ALANYL AMINOPEPTIDASE INHIBITORS AND PHARMACEUTICAL COMPOSITIONS CONTAINING SAID INHIBITORS

The present invention relates to the use of one inhibitor or of several inhibitors of alanyl aminopeptidases and/or of enzymes having a similar substrate specificity, for inducing the production of TGF-β1 and the expression of TGF-β1 in and/or on Treg cells and such use for preventing and/or treating autoimmune diseases, allergies, arteriosclerosis and for suppressing a graft rejection reaction. Furthermore, the invention relates to uses of such inhibitors, where peptide fragments of pathogenic autoantigens or synthetic analogs and/or specific antigenic components of pathogenic microorganisms are used in addition. The joint application of inhibitors of the above-mentioned enzymes and of antigens specific for a disease enhances the effect of said inhibitors directed against pathogenic T-cell clones and is suitable for a specific therapy of diseases caused by immunologic conditions.

It is already known that the course of diseases having an autoimmune pathogenesis, as for example diabetes mellitus type I or multiple sclerosis, is based on, or consists of, an activation and proliferation of autoreactive immune cells (i.e. immune cells directed against antigens of the own body), particularly of autoreactive T-lymphocytes. Similar mechanisms prevail in the generation of a rejection reaction after organ transplantations, but with the difference that, in the latter case, not "autoantigens", but "foreign antigens" of the donor organ are primarily responsible for a development of the fatal immune response. In both cases, i.e. in cases of autoimmune diseases and in cases of graft rejection reactions as well, there is an undesired break of "tolerance" of the immune system towards the antigens being either those of the own body or those emerging from the graft organ. A similar explanation is valid for the excessive immune response in allergic diseases.

FIG 1. Inhibition of autoreactive T-cells via soluble (a) or membrane-located TGF-β1 (b). Membrane-located TGF-β1 on Treg has a direct inhibitory effect on autoreactive T-cells by binding to their TGF-β1 receptor (cell-cell-contact) (top of (b)). Such a cell contact may be achieved by a simultaneous binding of Treg and of autoreactive T-cells as well to an antigen-presenting cell (APC, particularly dendritic cells) (top). On the other hand, APC may be changed by previous binding of Treg to the APC (absence of co-stimulating signals) in such a way that an autoreactive T-cell bound thereafter is not activated (anergia). In both cases, Treg and autoreactive T-cell are characterized by the same antigen specifity. (Figure from "Nature Reviews in Immunology 2:46-53 (2002)").

Scientific findings of the recent years show that such a "tolerance" is maintained in a healthy body by suppressing autoreactive T-lymphocytes actively with respect to their function and their growth. This is achieved by a specific suppressing T-cell population, i.e. the so-called natural regulatory T-cells (Treg, CD4+CD25+ cells). Treg cells are generated in the thymus gland [K. Kawahata et al., J. Immunol. 168:4399-4405, 2002] and make up a portion of 5 to 10% of the T-cells in the peripheric blood. They have an inhibitory effect on CD4+ T-cells of the same antigen specificity through a direct cell contact. Such an inhibitory effect is achieved by a strong expression of TGF-β1 in/on the Treg. The TGF-β1 is presented on the surface of the Treg and binds to the TGF-β1 receptor on autoreactive T-cells; this is a completely new mechanism of action of this strong immunosuppressive cytokine [Nakamura et al., J. Exp. Med. 194:629-644, 2001].

Treg cells inhibit autoimmunity more efficiently than the immune response against "foreign" antigens [P. Romagnoli et al., J. Immunol. 168:1644-1648, 2002]. Hence, restrictions or losses of functions of Treg cells have particular pathogenetic importance for the generation of autoimmune diseases. A direct connection between number/function of Treg cells and the manifestation of autoimmune diseases was shown for diabetes type I [S. Boudali et al., Eur. Cytokine Netw. 13:29-37, 2002]; S. Gregory et al., Diabetes 51:1367-1374, 2002], autoimmune encephalomyelitis (animal model of multiple sclerosis) [G. C. Furtado et al., Immunol. Rev. 182, 122-134, 2001; S. Muhallab et al., Scand. J. Immunol. 55, 264-273, 2002; N. H. Hamilton et al., Scand. J. Immunol. 55, 171-177, 2002], for the "autoimmune ovarian disease" (AOD) [K. S. Tung et al., Immunol. Rev. 182:135-148, 2001] as well as for Morbus Crohn [M. F. Neurath et al., J. Exp. Med. 195:1129-1143, 2002].

Moreover, Treg cells are responsible, too, for the suppression of intestinal or pulmonal inflammations [B. Singh et al., Immunol. Rev. 182, 190-200, 2001; S. Hori et al., Eur. J. Immunol. 32:1282-1291, 2002]. In the same way, the role of Treg cells in the suppression of rejection reactions after an allogenic (foreign) organ transplantation is proved unequivocally [C. I. Kingsley et al., J. Immunol. 168:1080-1086, 2002; P. A. Taylor et al., Blood 99:3493-3499, 2002; E. Chiffoleau et al., J. Immunol. 168:5058-5069, 2002]. Common to all those immune-suppressing functions of Treg cells is that they are characterized by a high antigen specificity, i.e. each clone of Treg cells is directed against a specific antigen and inhibits autoreactive T-cells of the same antigen specificity under normal physiological conditions. In cases of immune diseases said function of the Treg cells is lost, and autoreactive clones of T-cells as those (in the case of diabetes type I) directed against proteins of the pancreatic Beta cell cause an outbreak of the autoimmune disease.

On the other hand, such an antigen specificity may be used therapeutically by increasing/enhancing the number/function of those cells or recover those cells by a targeted "antigen-specific" activation of Treg cells (or of dendritic cells activating those cells) in vivo or ex vivo. For achieving this aim, the oral application of "antigens" is suitable, too [Zhang et al., J. Immunol. 167:4245-4253, 2001]. The preparation of such antigens, however, is extremely time-consuming and cost-intensive, from a technical point of view, and is restricted to antigen-specific T-cell clones.

The particular role of TGF-β1 for a regulation of the immunological hyper-reactivity is emphasized by two recent publications which show that an overproduction of TGF-β1 in CD4+ cells effected by genetic manipulation is capable of suppressing the course of the disease. Since, in the case of asthma, Th2-cells are decisively involved in the pathogenesis, the function of pathogenic clones of Th2-cells may, thus, effectively be inhibited by a transgenic over-production of TGF-β1 [G. Hansen et al., J. Clin. Invest. 105:61-70, 2000; G. J. Thorbecke et al., Cytokine Growth Factor Rev. 11:89-96, 2000]. The disadvantage of these processes for inducing the production of TGF-β1 in CD4+ or Treg cells is that they require a genetic manipulation, which, on the one hand, is very expensive and, on the other hand, is not suitable for a pharmacological application to humans or animals.

Figure 1:
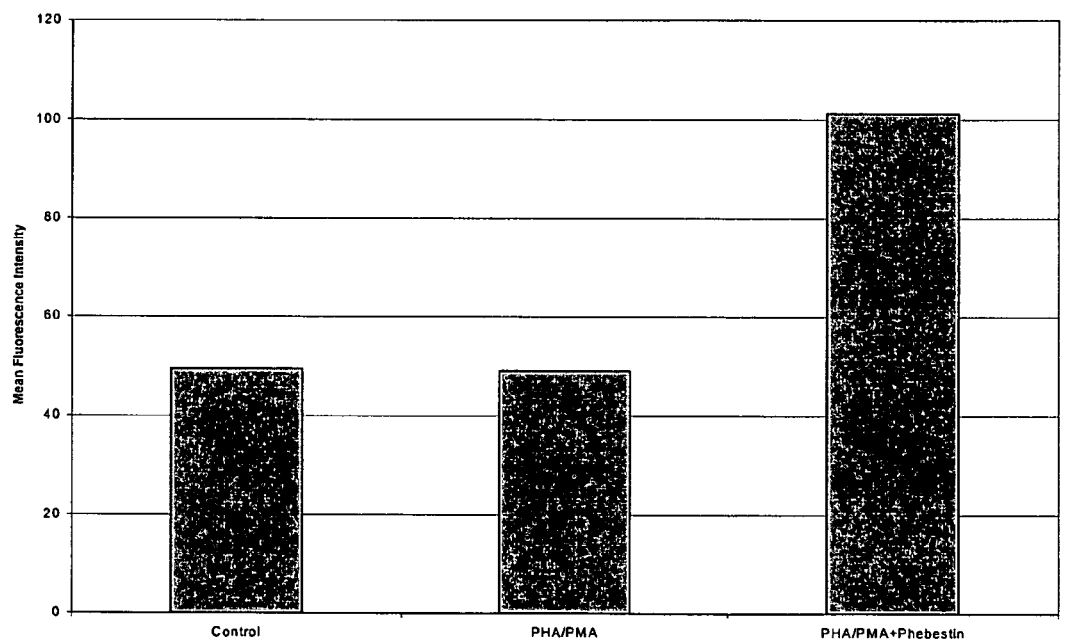
FIGS. 1-4 provide graphical depictions of data showing induction of TGF-⊕ expression for human T regulatory lymphocytes.

The present invention has the object to provide an efficient method for inducing the production and expression of TGF-$\beta$1 in and/or on Treg cells, which method, in addition, is suitable for a prevention and/or therapy of autoimmune diseases, allergies, arteriosclerosis and for a suppression of graft rejections in humans or animals. It is a further object to provide corresponding pharmaceutical preparations by means of which the above object can be achieved.

It was found surprisingly that inhibitors of alanyl aminopeptidases and/or of enzymes having a similar substrate specificity induce the production of TGF-$\beta$1 and the expression of TGF-$\beta$1 in and/or on Treg cells and, hence, are suitable for a prevention and treatment of autoimmune diseases, allergies, and arteriosclerosis and may serve a suppression of graft rejections.

Hence, the invention relates to the use of one inhibitor or of several inhibitors of alanyl aminopeptidases and/or of enzymes having a similar substrate specificity for an induction of the production of TGF-$\beta$1 and the expression of TGF-$\beta$1 in and/or on Treg cells.

The connection between the inhibition of alanyl aminopeptidases and/or the inhibition of enzymes having a similar substrate specificity and the induction of the production and surface expression of TGF-$\beta$1 in and/or on Treg cells was not known, up to now.

As the inhibitors, all inhibitors of alanyl aminopeptidases and all inhibitors of enzymes having a similar substrate specificity are possible. Preferably used are actinonin, leuhistin, phebestin, amastatin, bestatin, probestin, arphamenin, MR 387, $\beta$-amino thiols, $\alpha$-amino phosphinic acids and their esters and their salts, $\alpha$-amino phosphonates, $\alpha$-amino boronic acids, $\alpha$-amino aldehydes, hydroxamates of $\alpha$-amino acids, N-phenyl phthalimides, N-phenyl homophthalimides, $\alpha$-ketoamides, thalidomide and its derivatives. Particularly preferred among the above compounds are $\alpha$-ketoamides, $\alpha$-amino phosphinic acids, N-phenyl homophthalimides, $\alpha$-amino phosphonates and phebestin, wherein 3-amino-2-oxo-4-phenylbutanoic acid amides are particularly preferred as the $\alpha$-ketoamides, D-Phe-$\gamma$[PO(OH)—CH$_2$]-Phe-Phe are particularly preferred as the $\alpha$-amino phosphinic acid, PAQ-22 is particularly preferred as the N-phenyl homophthalimide, RB3014 and/or phebestin are particularly preferred as the $\alpha$-amino phosphonate, and PAQ-22, RB3014 and/or phebestin are used even more preferably.

The easy access, the low price and the simple processability with respect to galenics are particularly advantageous for the preferred and the especially preferred inhibitors.

As an enzyme having a similar substrate specificity as alanyl aminopeptidases, the cytosolic alanyl aminopeptidase is mentioned as an example. For the cytosolic alanyl aminopeptidase, PAQ-22 is a specific inhibitor. Hence, as the preferred inhibitor of the cytosolic alanyl aminopeptidase, PAQ-22 is used, or a mixture of several inhibitors is used which comprises PAQ-22.

The inhibition of the enzymatic activity of the membrane-located alanyl aminopeptidase (APN, CD13, E.C. 3.4.11.2) or the inhibition of enzymes having a similar substrate specificity or inhibitor sensitivity (as, for example, the cytosolic alanyl aminopeptidase, zAAP, PSA, E.C. 3.4.11.14) increases the gene expression of TGF-$\beta$1 in Treg cells as well as the expression of the immunosuppressive cytokine TGF-$\beta$1 ("transforming growth factor $\beta$1") in/on regulatory cells. Such an induction of the production and, in particular, of the surface expression of TGF-$\beta$1 on the Treg cells selectively effects a strengthening and restitution of the function of the Treg cells and, due to the above-mentioned connection between the expression of TGF-$\beta$1 on the Treg cells and the inhibitory effect on autoreactive T-lymphocytes, is suitable to overcome the existing functional deficits of the Treg cells in the course of autoimmune diseases and of inflammatory diseases, of allergies as well as of graft rejection reactions after organ transplantation and, hence, to allow the prevention of those diseases and/or to improve the course and the severity of those diseases and/or to cure those diseases. All those diseases, and the rejection reactions after organ transplantations as well, are characterized by the lack of a sufficiently effective natural immunosuppressive principle, i.e. not sufficiently functioning immunoregulatory cells including a deficient production of TGF-$\beta$1. The induction of TGF-$\beta$1 according to the invention is not restricted to single antigen-specific clones of T-cells.

Hence, the invention also relates to the use of one inhibitor or of several inhibitors of alanyl aminopeptidases and/or of enzymes having a similar substrate specificity for the prevention and/or treatment of autoimmune diseases. Preferred in accordance with the invention is the use for a prevention and/or treatment of rheumatoid arthritis, Lupus Erythematodes, multiple sclerosis, IDDM (insuline dependent diabetes mellitus), Morbus Crohn, Colitis Ulcerosa, psoriasis, neurodermatosis, glomerulonephritis, interstitial nephritis, vasculitis, autoimmune diseases of the thyroid gland, autoimmune-hemolytic anemia or other chronic diseases having an inflammatory genesis as, for example, arteriosclerosis. Particularly preferred is a use for preventing and/or treating multiple sclerosis or arteriosclerosis.

In accordance with the invention, one inhibitor or several inhibitors of alanyl aminopeptidases and/or of enzymes having a similar substrate specificity are also used for a prevention and/or treatment of allergies of the type I (according to Gell and Coombs) or of allergies of the types II, III or IV. In this connection, a use for the prevention and/or treatment of bronchial asthma or hay fever as the allergy of the type I (according to Gell and Coombs) and/or of contact allergies as the allergies of the types II, III and IV is preferred.

Moreover, the invention relates to the use of one inhibitor or of several inhibitors of alanyl aminopeptidases and/or of enzymes having a similar substrate specificity or a suppression of graft rejection reactions, preferably in the course of transplantation surgery of the kidneys or of the bone marrow.

In the prevention and/or treatment of autoimmune diseases, allergies and hay fever and in the suppression of graft rejection reactions, all inhibitors of alanyl aminopeptidases and all inhibitors of enzymes having a similar substrate specificity are considered to be suitable inhibitors. Preferred inhibitors used are actinonin, leuhistin, phebestin, amastatin, bestatin, probestin, arphamenin, MR387, $\beta$-amino thiols, $\alpha$-amino phosphinic acids and their esters and their salts, $\alpha$-amino phosphonates, $\alpha$-amino boronic acids, $\alpha$-amino aldehydes, hydroxamates of α-amino acids, N-phenyl phthalimides, N-phenyl homophthalimides, α-ketoamides, thalidomide and its derivatives. Particularly preferred among the above compounds are α-ketoamides, α-amino phosphinic acids, N-phenyl homophthalimides, α-amino phosphonates and phebestin, wherein 3-amino-2-oxo-4-phenylbutanoic acid amides are particularly preferred as the α-ketoamides, D-Phe-γ[PO(OH)—CH$_2$]-Phe-Phe are particularly preferred as the α-amino phosphinic acid, PAQ-22 is particularly preferred as the N-phenyl homophthalimide, RB3014 and/or phebestin are particularly preferred as the α-amino phosphonate, and PAQ-22, RB3014 and/or phebestin are used even more preferably.

As an enzyme having a similar substrate specificity as alanyl aminopeptidases, the cytosolic alanyl aminopeptidase is mentioned as an example. For the cytosolic alanyl aminopeptidase, PAQ-22 is a specific inhibitor. Hence, as the preferred inhibitor of the cytosolic alanyl aminopeptidase, PAQ-22 is used, or a mixture of several inhibitors is used which comprises PAQ-22.

Due to the high antigen specificity of the Treg cell clones, the joint application of aminopeptidase inhibitors and of the respective antigens causing the disease, for example antigenic peptides of the "myelin basic protein" for the case of multiple sclerosis, appears to be particularly suitable for a therapy, since an inhibition of the pathogenic cell clones is effected in a targeted and specific manner on this route. The antigen-specific immunosuppression is virtually free of side effects [Zhang et al., J. Immunol. 167:4245-4253, 2001].

Hence, the invention also relates to the use of inhibitors of alanyl aminopeptidases and/or of enzymes having a similar substrate specificity for an induction of the production of TGF-β1 and of the expression of TGF-β1 in and/or on Treg cells and for a prevention and/or treatment of autoimmune diseases, allergies, hay fever, arteriosclerosis as well as for a suppression of graft rejection reactions, wherein peptide fragments of pathogenic autoantigens or synthetic analogs and/or specific antigenic components of pathogenic microorganisms are used in addition. The above-mentioned inhibitors in question and the preferred inhibitors and particularly preferred inhibitors as well as the preferred and particularly preferred diseases are also preferred in the use where peptide fragments of pathogenic autoantigens or synthetic analogs and/or specific antigenic components of pathogenic microorganisms are used in addition. Preferred peptide fragments of pathogenic autoantigens for multiple sclerosis are MBP (myelin basic protein), MOG (myelin oligo-dendrocyte glycoprotein), MAG (myelin-associated glycoprotein) and PLP (proteolipid protein). Preferred specific antigenic components of pathogenic microorganisms are sheath proteins or membrane glycolipide complexes.

The easy access, the low price and the simple processability with respect to galenics are particularly advantageous for the preferred and the especially preferred inhibitors.

Hence, the invention also relates to the use of one inhibitor or of several inhibitors of alanyl aminopeptidases and/or of enzymes having a similar substrate specificity for the manufacture of a medicament or of a pharmaceutical preparation for an induction of the production of TGF-β1 and of the expression of TGF-β1 in and/or on Treg cells.

As the inhibitors, all inhibitors of alanyl aminopeptidases and all inhibitors of enzymes having a similar substrate specificity are possible. Preferably used are actinonin, leuhistin, phebestin, amastatin, bestatin, probestin, arphamenin, MR 387, β-amino thiols, α-amino phosphinic acids and their esters and their salts, α-amino phosphonates, α-amino boronic acids, α-amino aldehydes, hydroxamates of α-amino acids, N-phenyl phthalimides, N-phenyl homophthalimides, α-ketoamides, thalidomide and its derivatives. Particularly preferred among the above compounds are α-ketoamides, α-amino phosphinic acids, N-phenyl homophthalimides, α-amino phosphonates and phebestin, wherein 3-amino-2-oxo-4-phenylbutanoic acid amides are particularly preferred as the α-ketoamides, D-Phe-γ[PO(OH)—CH$_2$]-Phe-Phe are particularly preferred as the α-amino phosphinic acid, PAQ-22 is particularly preferred as the N-phenyl homophthalimide, RB3014 and/or phebestin are particularly preferred as the α-amino phosphonate, and PAQ-22, RB3014 and/or phebestin are used even more preferably.

As an enzyme having a similar substrate specificity as alanyl aminopeptidases, the cytosolic alanyl aminopeptidase is mentioned as an example. For the cytosolic alanyl aminopeptidase, PAQ-22 is a specific inhibitor. Hence, as the preferred inhibitor of the cytosolic alanyl aminopeptidase, PAQ-22 is used, or a mixture of several inhibitors is used which comprises PAQ-22.

The invention also relates to the use of one inhibitor or of several inhibitors of alanyl aminopeptidases and/or of enzymes having a similar substrate specificity for the preparation of a medicament or of a pharmaceutical preparation for the prevention and/or treatment of autoimmune diseases, of allergies of the type I (according to Gell and Coombs) as, for example, hay fever, of allergies of the types II, III or IV, and also relates to the use for the preparation of a medicament or of a pharmaceutical preparation for suppressing graft rejection reactions. Preferred diseases and types of transplantations are mentioned in the sub-claims 26, 27, 29 and 31. Preferred inhibitors of alanyl aminopeptidases and of enzymes having a similar substrate specificity are set forth in claims 32 to 35.

When using one inhibitor or several inhibitors of alanyl aminopeptidases and/or of enzymes having a similar substrate specificity for preparing a medicament or a pharmaceutical preparation for the prevention and/or treatment of autoimmune diseases, of allergies of the type I (according to Gell and Coombs) as, for example, hay fever, of allergies of the types II, III or IV, and for preparing a medicament or a pharmaceutical preparation for suppressing graft rejection reactions, peptide fragments of pathogenic autoantigens for multiple sclerosis or synthetic analogs and/or specific antigenic components of pathogenic microorganisms may be used in addition, wherein MBP (myelin basic protein), MOG (myelin oligo-dendrocyte glycoprotein), MAG (myelin-associated glycoprotein) and/or PLP (proteolipid protein) are preferably used as peptide fragments of pathogenic autoantigens, and sheath proteins or membrane glycolipide complexes are used as specific antigenic components of pathogenic microorganisms.

In addition, the present invention relates to a pharmaceutical preparation comprising one inhibitor or several inhibitors of alanyl aminopeptidases and/or of enzymes having a similar substrate specificity as well as one or more than one pharmacologically unobjectionable carrier, additive and/or auxiliary substanc(es). The invention also relates to a pharmaceutical preparation comprising one inhibitor or several inhibitors of alanyl aminopeptidases and/or of enzymes having a similar substrate specificity and peptide fragments of pathogenic autoantigens or synthetic analogs and/or specific antigenic components of pathogenic microorganisms as well as one or more than one pharmacologically unobjectionable carrier, additive and/or auxiliary substanc(es).

The invention shows that the application of inhibitors of the above enzymes or of corresponding pharmaceutical preparations and administration forms thereof are suitable for a therapy of inflammatory diseases and autoimmune diseases as well as of allogenic rejection reactions and of allergies, for the generation of which the proliferation and the activation of pathogenic T-cell clones has a central importance. The simultaneous application of antigens specific for the respective disease enhances such an effect additionally and restricts the effects to the process of pathogenic relevance.

The application of aminopeptidase inhibitors for the induction of the TGF-β1 expression in/on Treg cells and, hence, for an enhancement of the immunosuppressive function of this pathogenetically important inhibitory T-cell population is a novel method and a supplementary form of therapy meshing with the central pathogenetical process in connection with the above-mentioned diseases.

The inhibitor or the several inhibitors of alanyl aminopeptidases may be applied in pharmaceutically applicable formulation complexes as inhibitors, substrates, pseudosubstrates, inhibitor-effective peptides and peptide derivatives as well as antibodies to said enzyme. Preferred inhibitors are bestatin, phebestin, probestin, actinonin, leuhistin, RB3014, PAQ-22, and their derivatives, and particularly preferred are phebestin, RB3014 and/or PAQ-22.

The administration may occur in all suitable forms as, for example, topical application in the form of cremes, ointments, pastes, gels, solutions, sprays, liposomes, lotions (shaken mixtures), hydrocolloid dressings, and other dermatological bases/vehicles including the instillative application, or as systemic application for the oral, transdermal, intravenous, subcutaneous, intracutaneous, inhalative, intramuscular application in suitable preparations and suitable galenic forms or bound to, or included into, microparticles for passing the blood brain barrier. Simultaneously, the application of antigens "specific" for a certain disease (peptide fragments, lipopolysaccharides, etc.) in corresponding administration forms may improve the success of a therapy.

The present invention is explained in more detail in the subsequent examples; however, the invention is not restricted to the examples which follow.

EXAMPLE 1

Induction of the Surface Expression of TGF-β1 on Human Regulatory T-Lymphocytes (CD4$^+$CD25$^+$) After Incubation with the Inhibitor Phebestin The T-cells were incubated for 24 h without adding (control), with adding PHA and PMA and with simultaneously adding PHA/PMA and phebestin. PHA (phythemagglutinine) and PMA (phorbol myristate acetate) were used as mito-gens and agents stimulating the proliferation. Subsequently, the surface expression of TGF-β1 was measured by flow cytometry using a commercially available polyclonal anti-TGF-β1 antibody (chicken anti-human; R & D Systems). The results are shown in FIG. 1.

EXAMPLE 2

Figure 2:
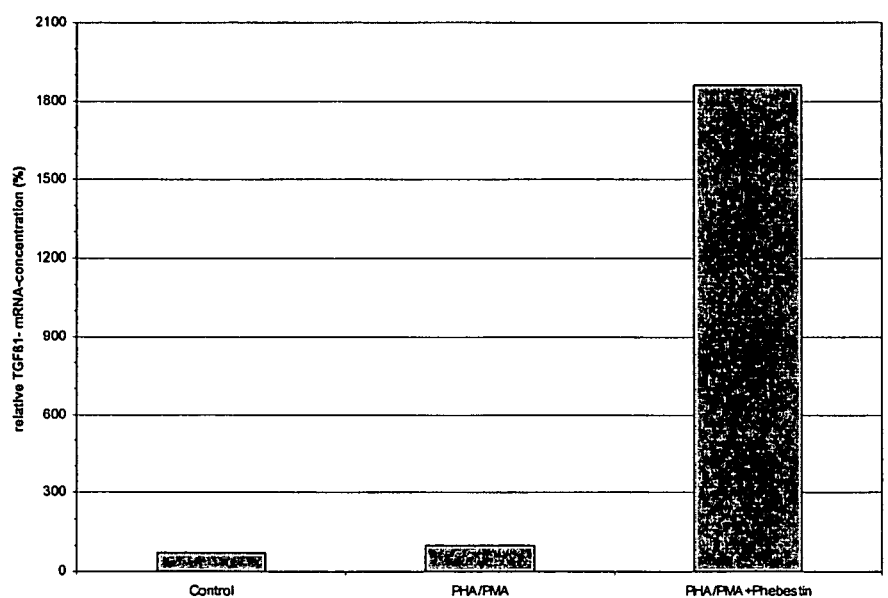

Induction of the Gene Expression of TGF-β1 in Human Regulatory T-Lymphocytes (CD4$^+$CD25$^+$) After an Incubation with the Inhibitor Phebestin The T-cells were incubated for 24 h without adding (control), with adding PHA and PMA or with simultaneously adding PHA/PMA and phebestin. PHA (phythemagglutinine) and PMA (phorbol myristate acetate) were used as mito-gens and agents stimulating the proliferation. Subsequently, the content of TGF-β1-mRNA was determined by quantitative RT-PCR and using the i-cycler. The results are shown in FIG. 2.

EXAMPLE 3

Induction of the Gene Expression of TGF-β1 in Human Regulatory T-Lymphocytes (CD4$^+$CD25$^+$) after an incubation with the inhibitor PAQ-22

Figure 3:
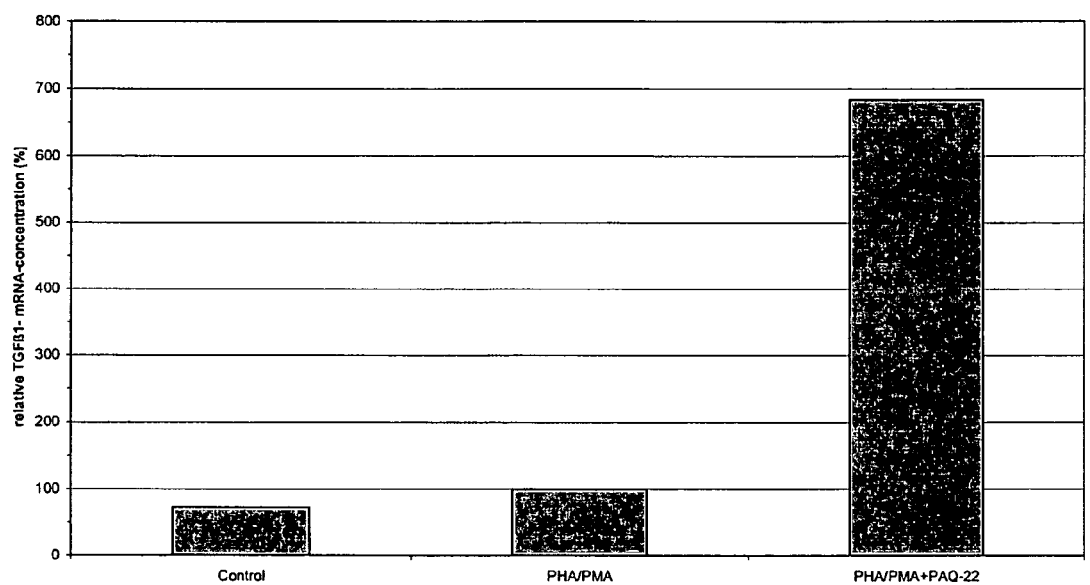

The T-cells were incubated for 24 h without adding (control), with adding PHA and PMA and with simultaneously adding PHA/PMA and PAQ-22. PHA (phythemagglutinine) and PMA (phorbol myristate acetate) were used as mito-gens and agents stimulating the proliferation. Subsequently, the content of TGF-β1-mRNA was determined by quantitative RT-PCR and using the i-cycler. The results are shown in FIG. 3.

EXAMPLE 4

Induction of the Gene Expression of TGF-β1 in Human Regulatory T-Lymphocytes (CD4$^+$CD25$^+$) After an Incubation with the Aminopeptidase Inhibitor RB3014

Figure 4:
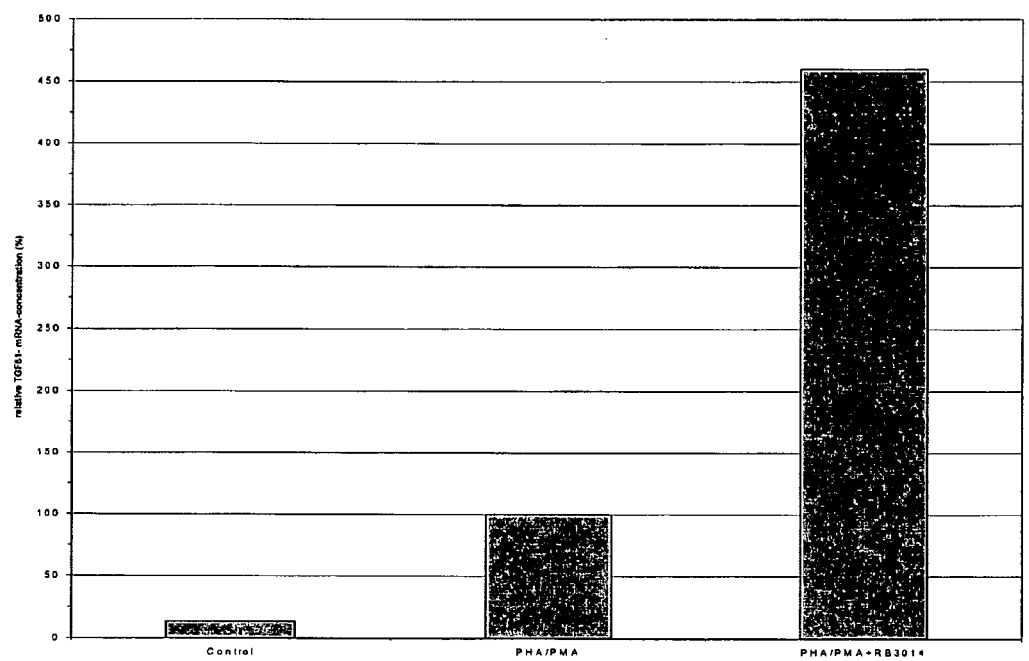
Figure 5:
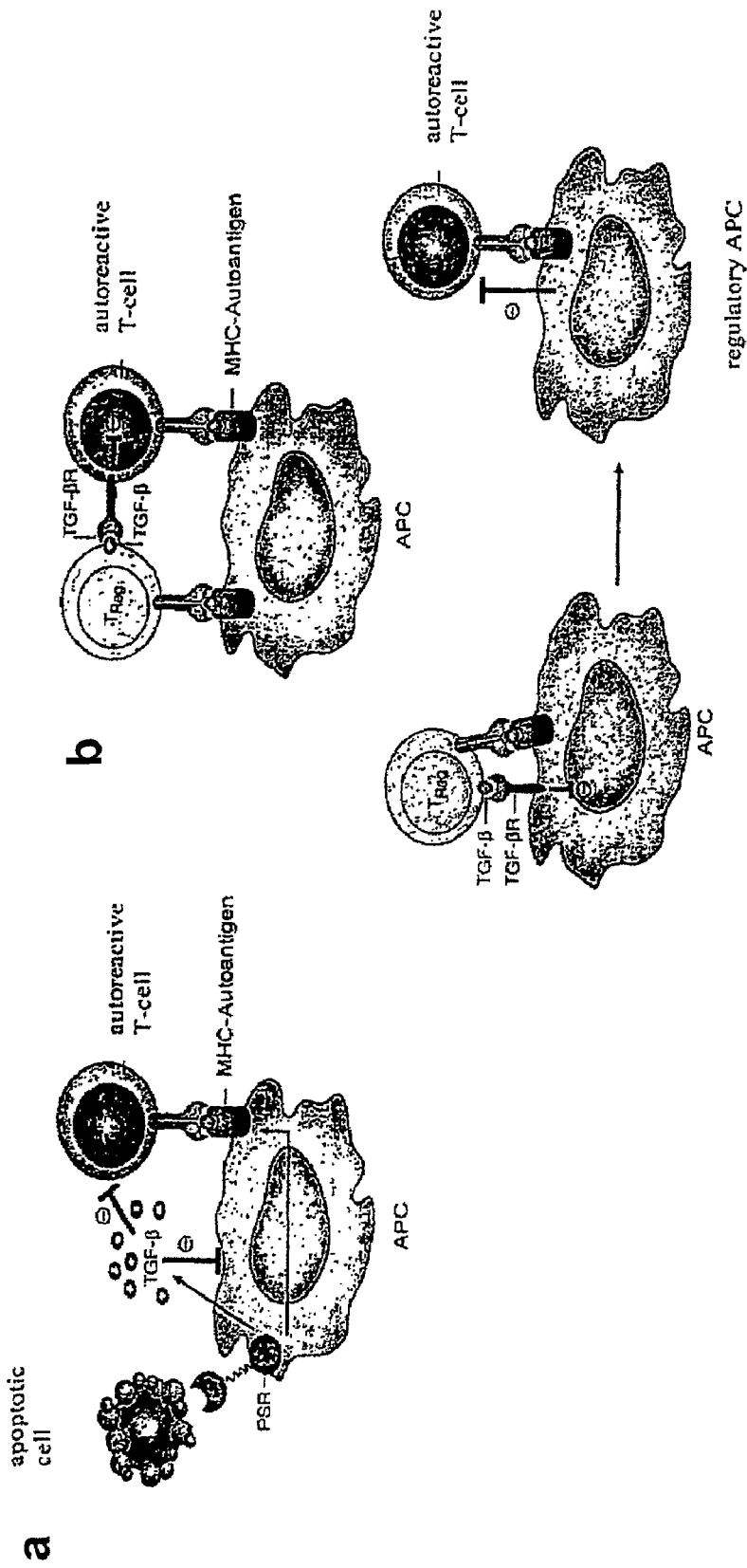
FIG. 5 provides a graphical representation of inhibition of autoreactive T-cells via soluble (a) or membrane-located TGF-⊕1 (b). Membrane-located TGF-⊕1 on Treg has a direct inhibitory effect on autoreactive T-Cells by binding to their TGF-⊕1 receptor (cell-cell-contact) (top of(b)). Such a cell contact may be achieved by a simultaneous binding of Treg and of autoreactive T-cells as well to an antigen-presenting cell (APC, particularly dendritic cells) (top). On the other hand, APC may be changed by previous binding of Treg to the APC (absence of co-stimulating signals) in such a way that an autoreactive T-cell bound thereafter is not activated (anergia). In both cases, Treg and autoreactive T-cell are characterized by the same antigen specificity. (Figure from "Nature Review in Immunology 2: 46-53 (2002)").

The T-cells were incubated for 72 h without adding (control), with adding PHA and PMA and with simultaneously adding PHA/PMA and RB3014. PHA (phythemagglutinine) and PMA (phorbol myristate acetate) were used as mito-gens and agents stimulating the proliferation. Subsequently, the content of TGF-β1-mRNA was determined by quantitative RT-PCR and using the i-cycler. The results are shown in FIG. 4.

The invention claimed is:

1. A method for treating an autoimmune disease selected from the group consisting of rheumatoid arthritis and Lupus Erythematodes comprising administering to an individual in need of treatment a composition comprising an inhibitor of alanyl aminopeptidase, wherein the inhibitor of alanyl aminopeptidase is selected from the group consisting of phebestin, PAQ-22, and combinations thereof.

2. The method of claim 1, wherein the inhibitor of alanyl aminopeptidase is phebestin.

3. The method of claim 1, wherein the inhibitor of alanyl aminopeptidase is PAQ-22.

4. The method of claim 1, wherein the individual is treated for rheumatoid arthritis.

5. The method of claim 1, wherein the individual is treated for Lupus Erythematodes.

6. The method of claim 2, wherein the individual is treated for rheumatoid arthritis.

7. The method of claim 2, wherein the individual is treated for Lupus Erythematodes.

8. The method of claim 3, wherein the individual is treated for rheumatoid arthritis.

9. The method of claim 3, wherein the individual is treated for Lupus Erythematodes.

* * * * *